United States Patent [19]

Linkow et al.

[11] Patent Number: 5,165,892
[45] Date of Patent: Nov. 24, 1992

[54] NECKLESS BLADE IMPLANT

[76] Inventors: Leonard I. Linkow, 1530 Palisades Ave., Fort Lee, N.J. 07024; Michael A. Gambale, 155 Webster St., West Hanover, Mass. 02339

[21] Appl. No.: 595,953

[22] Filed: Oct. 11, 1990

[51] Int. Cl.$^5$ .............................................. A61C 8/00
[52] U.S. Cl. ................................................ 433/176
[58] Field of Search ................ 433/173, 174, 175, 176

[56] References Cited

U.S. PATENT DOCUMENTS

| | | | |
|---|---|---|---|
| 4,178,686 | 12/1979 | Riess et al. | 433/201.1 |
| 4,600,388 | 7/1986 | Linkow | 433/176 |
| 4,661,066 | 4/1987 | Linkow et al. | 433/176 |
| 4,799,886 | 1/1989 | Wimmer | 433/176 |
| 4,931,016 | 6/1990 | Sillard | 433/174 X |

Primary Examiner—John J. Wilson
Assistant Examiner—Jeffrey A. Smith
Attorney, Agent, or Firm—Darby & Darby

[57] ABSTRACT

An oral implant for supporting an artificial tooth structure has an implant portion adapted to be fitted in an opening in a bone in the vicinity of the occlusal plane of a patient in such a manner that at least a part of the connection part extends beyond a rim of the opening in the bone or can remain just below the bone while the base of the post rests on the bone. There is at least one post portion having first and second ends. The first end is adapted to receive at least a part of the artificial tooth structure. The second end is adapted for a direct connection to the connection part of the implant portion. The past may be connected to the implant portion by an arrangement in which the implant portion has an opening along the upper surface. Ridges are provided along the sides of the opening and a center projection extends up from the base of the opening. The post portion has complementary channels and openings for receiving the ridges and projection.

6 Claims, 2 Drawing Sheets

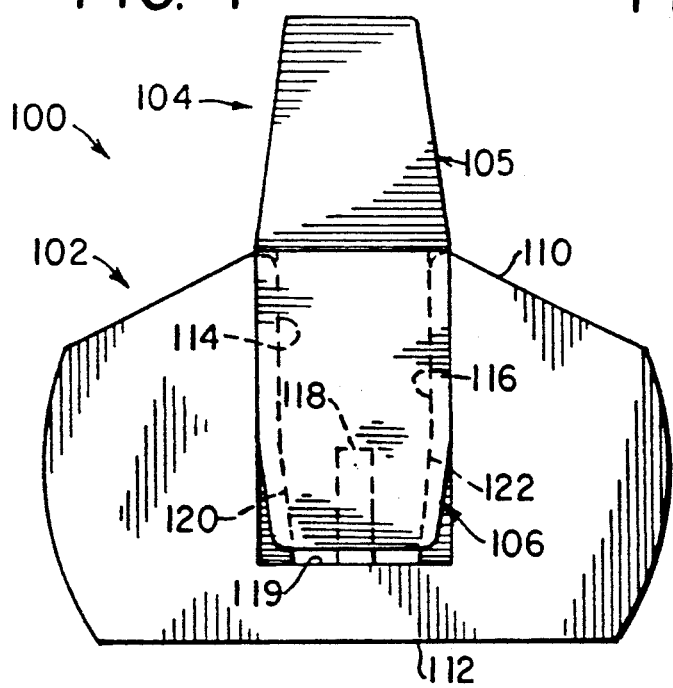
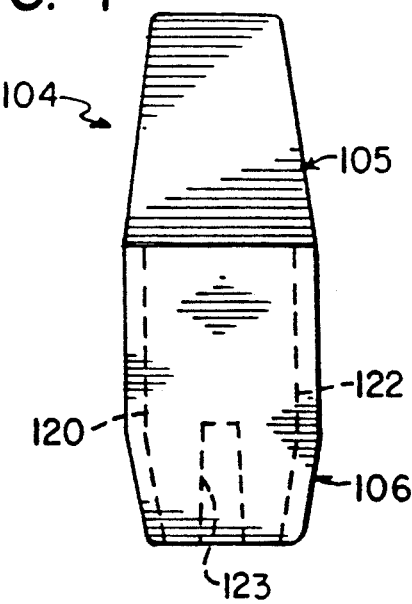
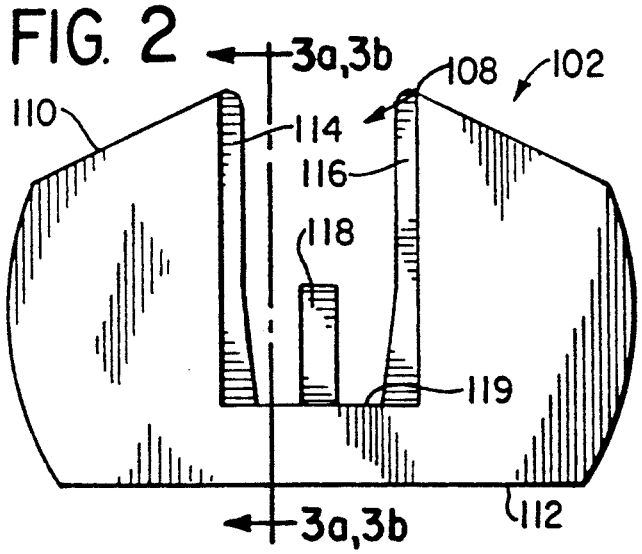
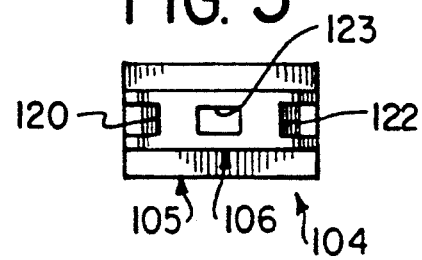
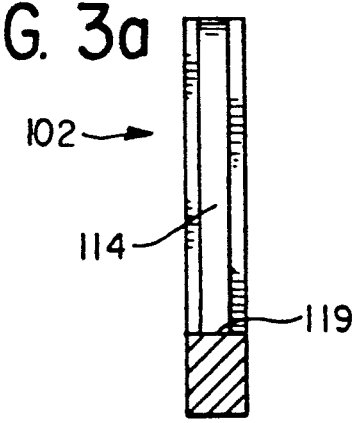
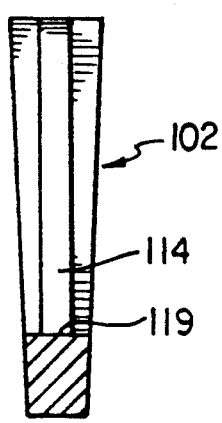

NECKLESS BLADE IMPLANT

BACKGROUND OF THE INVENTION

This invention relates to dental implants and, more particularly, to neckless blade implants.

A dental implant such as that described in U.S. Pat. Nos. 3,465,441 and 3,660,899 of the present inventor are used to support an artificial bridge, tooth or other dental prosthesis. The implant has an implant portion, e.g. in the form of a blade, that is secured in the underlying bone in an edentulous span. A post portion, typically with a recessed neck part, extends up form the implant portion and supports the artificial bridge or crown. This type implant is inserted by making an incision in the fibromucosal tissue down to the underlying alveolar ridge crest bone. The tissue is then reflected to expose the bone and a burr is used to create a groove in the bone which is as deep as the implant portion. The implant portion is then wedged into the bone. After the insertion, the tissue is sutured about the neck part so that the rest of the post protrudes above the tissue line. Typically, a few weeks or months are allowed to pass before the dental prosthesis is attached to the post. During this period, bone starts to grow around the implant portion and through holes provided in it, thereby acting to anchor the implant in place before it is stressed by use.

Submergible blade implants, such as that shown in U.S. Pat. No. 4,177,562 of A. L. Miller and A. J. Viscido, allow a blade to be inserted in the jawbone for a long period of time before being placed in actual use. With this type of implant the blade is completely submerged in the bone. It is then covered over and allowed to remain in place for several months. For this period it is protected against being dislodged by the tongue or other teeth during mastication. Once there has been substantial regrowth of the bone over, around and through the submerged blade, the tissue is again opened and the post is attached to the blade by a typical screw connection.

As noted, it is common for many types of oral implants disclosed by the prior art to have a post with a neck portion which connects to a blade. Such a neck portion is typically much narrower than the rest of the post and the blade. In view of that, a step-type transitioned area is defined between the post and the blade. Steep variation between the dimensions of the blade, post and the neck makes the transitioned area subject to a much greater concentration of the stresses than other areas of the implant. All this makes the design of the narrow neck the weak spot of the oral implants disclosed by the prior art. In use, such implants can bend in the area of the neck portion when chewing movements are performed. This might cause bone resorption immediately below the neck portion and cause the neck to break.

U.S. Pat. No. 4,178,686 to Riess et al. provides an oral implant in which the implant portion is a polymer matrix having spherical particles of tricalciumphosphate ceramic embedded in its exterior. A post portion has an elongated core member extending substantially into the implant portion. The base of the top part of the post portion extends to the outer edges of the implant portion and tapers inward in the part towards the artificial tooth support. The tooth support itself may be attached to the post by means of a threaded shaft. With this arrangement, the forces of mastication are resisted solely by the threaded shaft, which is relatively narrow, and/or the narrow core portion of the post.

U.S. Pat. No. 4,600,388 to Leonard Linkow, one of the coinventors of the present invention, discloses a blade in which the post is designed to straddle recessed portions in the blade. Because of these recessed portions in the blade, the post does not extend beyond the outer limits of the blade. Further, the legs of the implant, that allow it to straddle the blade, are relatively thin and these thin legs must resist the forces of mastication. Further, there is no direct means for rigidly securing the post to the blade, other than the nature spring force of the legs of the post.

The relatively narrow neck portions of posts in prior art implants are subject to bending and breakage during normal use. When this occurs it is often necessary to remove part or all of the implant, including the blade portion, to repair the damage. Thus, it would be extremely advantageous if blade implants could be provided with extremely rugged post portions which could easily resist the forces of mastication.

SUMMARY OF THE INVENTION

The present invention provides an oral blade-type implant for supporting an artificial tooth structure in which (a) the traditional recessed neck portion of the support post is eliminated, and (b) one end of the post is adapted for a direct connection to the blade and has a width and length such that the post base extends outwardly from sides of the blade, thus defining shoulders for support of the artificial dental structure.

In an illustrative embodiment of the invention, the post portion is detachably connected to the implant portion. The implant portion has a generally U-shaped opening along its top edge. The opening has ridges along its vertical sides and a center projection extending from the horizontal base of the opening. The post portion has channels on each side for receiving the ridges, and a hole in its bottom for receiving the center projection. This arrangement for attaching the post reduces stress points which exist in the screw implant. Stress points can cause fatigue cracks.

BRIEF DESCRIPTION OF THE DRAWINGS

Other advantages and features of the invention are described with reference to exemplary embodiments, which are intended to explain and not to limit the invention, and are illustrated in the drawings in which:

FIG. 1 is a front view of a still further embodiment of the dental implant with the post installed;

FIG. 2 is a front view of the implant portion of the dental implant shown in FIG. 1 without the post;

FIG. 3 is a cross-sectional view along line 23—23 of FIG. 2;

FIG. 4 is a side view of the post portion of the dental implant shown in FIG. 1;

FIG. 5 is a bottom view of the post portion shown in FIG. 4;

DESCRIPTION OF ILLUSTRATIVE EMBODIMENT

Figure 6:
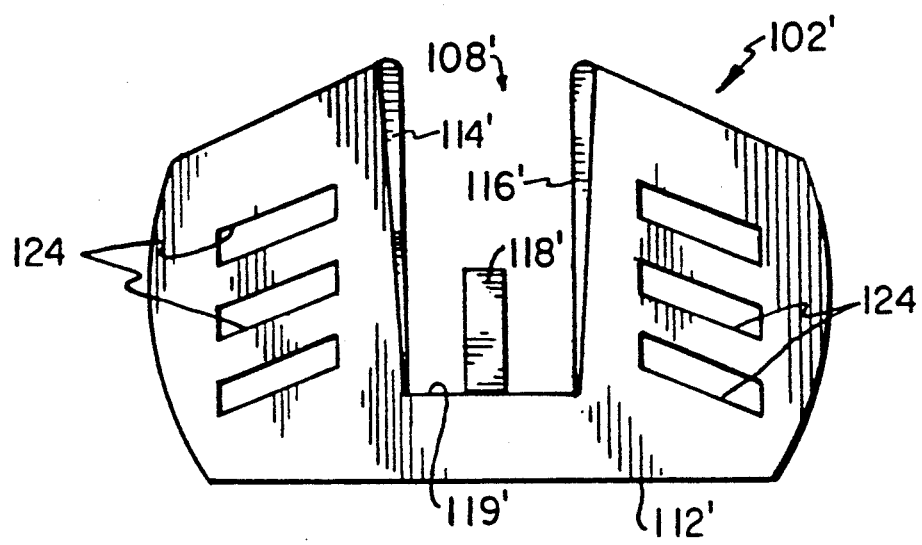
FIG. 6 is a front view of a further embodiment of the implant portion of the dental implant according to the present invention.

Although a specific embodiment of the invention will now be described with reference to the drawings, it should be understood that the embodiment shown is by way of example only and merely illustrative of but one of the many possible specific embodiments which can represent applications of the principles of the invention. Various changes and modifications, obvious to one skilled in the art to which the invention pertains, are deemed to be within the spirit, scope and contemplation of the invention as further defined in the appended claims.

FIG. 1 shows a detachable surgical dental implant according to the present invention. The surgical implant 100 has an implant portion 102 and a post portion 104. The implant portion 102 is adapted to be fitted into an opening in the bone of a patient in the vicinity of the occlusal plane. The width of the bottom of the implant portion 102 is sufficient so as to allow tight engagement with an opening in the patient's bone.

The post portion 104 is shown in FIG. 4 and has a first end 105 which receives at least a part of an artificial tooth structure (not shown). The post 104 also has a second end 106 which is adapted for direct connection with the implant portion 102 without any intermediary parts. This connection is made as wide as possible in the mesial-distal direction to prevent weaknesses in the post which can cause bending and consequential loss of bone due to the movement of the implant in the jaw.

The implant portion 102 has a generally U-shaped opening 108 along its top edge 110, as is seen in FIG. 2. The bottom edge 112 is sufficiently wide to allow tight engagement with the opening in the bone in which the implant portion 102 is inserted. Along the vertical edges of the opening 108 are mesial and distal ridges 114, 116, as shown in FIGS. 2, 3a and 3b. A center projection 118 extends upward from the center of the horizontal base 119 of the U-shaped opening 108.

The second end 106 of post portion 104 has mesial and distal channels 120, 122 (shown in FIG. 5) in its end surfaces for receiving the ridges 114, 116, and a hole 123 in its bottom for receiving the center projection 118 of the implant portion 102. This arrangement eliminates sharp stress points found in prior art screw implants which, for example, can lead to fatigue cracks. The opening 108 may narrow as it nears the horizontal base 119 so that the post portion 104 may be wedged onto the implant portion 102. (See FIG. 6)

The post portion 104 is vertically supported by the center projection 118 and is laterally supported by the mesial and distal ridge/channel combination which lock the post 104 onto the implant portion 102. This arrangement provides for a stable arrangement without the weak points found in the screw or narrow neck connection type dental implants.

Figure 7:
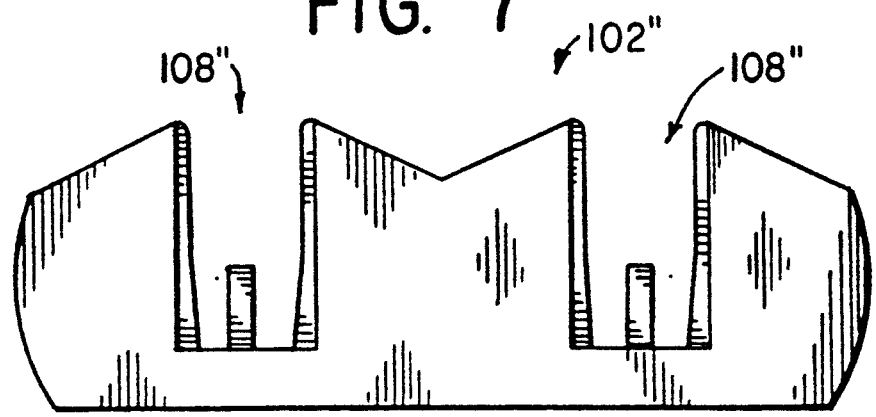
FIG. 7 is a front view of yet a further embodiment blade portion of the dental implant according to the present invention.

In another embodiment of the present invention, the implant portion 102 may have a wedge-shaped configuration with the narrow end at the bottom, as shown in FIG. 3b. This wedge shape is advantageous for establishing a high friciton engagement with the surrounding bone during installation of the implant 100 in the patient's jaw bone. As shown in FIG. 6, the implant portion 102' may include holes or vents 124 which allow bone to grow completely through the implant portion 102' so as to anchor the implant portion 102' in place. Also, the implants shown in FIGS. 1-6 are adapted to receive only a single post portion 104. However, a plurality of post portions 104 may be attached to the same implant portion, such as implant portion 102'' of FIG. 7.

The various parts of each embodiment may be made of titanium, vitalium, or surgical stainless steel.

The implant 100 is installed in the following manner. The surgeon makes an incision in the patient's gum tissue and exposes the bone. A groove is drilled in the bone deep enough for the implant portion 102 to be submerged in the groove below the upper rim of the bone so that only the apex or connecting part 103 of the implant portion 102 protrudes outwardly from the groove in the direction of the occlusal plane.

The apex 103 does not protrude above the gum tissue. When the implant portion 102 is in place, a healing cap, e.g., of plastics material, (not shown) is connected to the implant portion 102 as if it were the post portion 104. The cap is identically shaped to the post portion 104, except that it does not have the first end 105 for receiving the tooth structure. Only a very small part of the implant portion 102 protrudes above the bone. Therefore, the implant is protected from impact with the patient's tongue and teeth. The tissue is then sutured over the cap.

A period of time, typically a few months, is allowed to pass so bone may grow around and through (if vented) the implant portion 102. The cap prevents bone from growing through the U-shaped opening 108.

Once the implant portion 102 is firmly anchored in the bone, a new incision is made in the gum tissue and the cap is removed and the post portion 104 is attached to the implant portion 102.

As another alternative, the implant portion may be completely submergible below the rim of the bone during installation. Then bone may grow not only around, but over the top of the implant, except where the healing cap is located. In such a case, the end 106 of the post which is eventually installed is made slightly longer than the other posts so as to project end 105 above the rim of the bone.

What is claimed is:

1. An oral implant for supporting an artificial tooth structure, comprising:
    an implant portion adapted to be fitted in an opening in a bone structure in the vicinity of the occlusal plane of a patient;
    at least one post portion having first and second ends, said first end being adapted to receive at least a part of an artificial tooth structure and said second end being adapted for direct connection to said implant portion;
    one edge of said implant portion being adapted to receive said post portion in an opening having a mesial side and a distal side and a generally horizontal base, said mesial side and distal side each having a ridge and said horizontal base having a center projection; and
    said second end of said post portion being complementary in shape to said opening and having a mesial channel and a distal channel for receiving said ridges and a bottom gap receiving said center projection.

2. The oral implant of claim 1, wherein said opening is generally rectangular.

3. The oral implant of claim 1, wherein said opening narrows towards said horizontal base.

4. The oral implant of claim 1, wherein a cross section of the implant portion in the bucco-lingual direction has a wedge-shaped configuration with wide and narrow ends, said wide end located at said edge having said opening.

5. The oral implant of claim 1, wherein said implant portion has vents which allow bone to grow through said implant portion.

6. The oral implant of claim 1, wherein said implant portion is adapted to receive a plurality of post portions.

* * * * *